US006316383B1

United States Patent
Tacke et al.

(10) Patent No.: US 6,316,383 B1
(45) Date of Patent: *Nov. 13, 2001

(54) MOLDINGS BASED ON SILICA

(75) Inventors: Thomas Tacke, Paducah, KY (US); Peter Schinke, Rodenbach (DE); Hermanus Lansink Rotgerink, Glattbach (DE); Helmfried Kraus, Rodenbach (DE)

(73) Assignee: Degussa AG, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/344,488

(22) Filed: Jun. 25, 1999

(30) Foreign Application Priority Data

Jun. 26, 1998 (DE) ................................................ 198 28 491

(51) Int. Cl.[7] ............................. B01J 21/08; A47G 19/22; B28B 21/00; C04B 14/04; C04B 35/14

(52) U.S. Cl. ........................ 502/232; 502/233; 502/245; 502/262; 502/243; 502/250; 502/439; 502/527.14; 502/527.16; 428/34.4; 428/34.6; 106/482; 501/133

(58) Field of Search ..................................... 502/232, 233, 502/262, 245, 243, 250, 439, 527.14, 527.16; 428/34.4, 34.6; 106/482; 501/133; 264/629, 632, 634, 669, 670, 638, 177.11

(56) References Cited

U.S. PATENT DOCUMENTS

| | | | | |
|---|---|---|---|---|
| 3,905,775 | * | 9/1975 | Sowards et al. | 422/180 |
| 4,366,093 | * | 12/1982 | Shiozaki et al. | 502/439 |
| 4,510,263 | | 4/1985 | Pereira | 502/314 |
| 4,642,360 | * | 2/1987 | Nojiri et al. | 549/534 |
| 4,729,982 | * | 3/1988 | Thistlethwaite et al. | 502/338 |
| 4,853,351 | * | 8/1989 | Takahashi et al. | 501/87 |
| 4,869,944 | * | 9/1989 | Harada et al. | 428/116 |
| 5,086,031 | * | 2/1992 | Deller et al. | 502/251 |
| 5,166,120 | * | 11/1992 | Deller et al. | 502/225 |
| 5,250,487 | * | 10/1993 | Wirtz et al. | 502/243 |
| 5,332,710 | * | 7/1994 | Nicolau et al. | 502/243 |
| 5,571,771 | | 11/1996 | Abel | 502/330 |
| 5,776,240 | * | 7/1998 | Deller et al. | 106/482 |
| 5,777,156 | | 7/1998 | Abel | 560/245 |
| 5,808,136 | * | 9/1998 | Tacke et al. | 560/243 |
| 5,854,171 | * | 12/1998 | Nicolau et al. | 502/330 |
| 5,858,906 | * | 1/1999 | Deller et al. | 502/170 |
| 5,910,608 | * | 6/1999 | Tenten et al. | 562/632 |
| 5,968,860 | * | 10/1999 | Herzog | 502/5 |
| 5,972,824 | * | 10/1999 | Herzog et al. | 502/160 |

FOREIGN PATENT DOCUMENTS

| | | |
|---|---|---|
| 24 25 058 A1 | 12/1975 | (DE) . |
| 27 19 543 C2 | 12/1977 | (DE) . |
| 3803895-C1 * | 4/1989 | (DE) . |
| 3912504-A1 * | 10/1990 | (DE) . |
| 195 38 799 A1 | 4/1997 | (DE) . |
| 0 004 079 A2 | 9/1979 | (EP) . |
| 0 464 633 A1 | 1/1992 | (EP) . |
| 0 634 208 A1 | 1/1995 | (EP) . |
| 0 807 615 A1 | 11/1997 | (EP) . |

* cited by examiner

Primary Examiner—Mark L. Bell
Assistant Examiner—Patricia L. Hailey
(74) Attorney, Agent, or Firm—Pillsbury Winthrop LLP

(57) ABSTRACT

Moldings based on silica having a hollow cylindrical configuration with internal reinforcing stays or spokes leading from an inner wall of a hollow cylinder to the center of the molding or in the form of miniliths having passageway channels therethrough, are produced by homogenizing silica with methyl hydroxyethyl cellulose, wax and/or polyethylene glycol. Water and optionally aqueous alkaline ammonia solution are added, and the mixture is subjected to kneading and forming, extruding, optionally cutting the extrudate to the desired length by means of a cutting device, drying at a temperature from 20 to 150° C., and annealing for a period from 30 minutes to 10 hours at a temperature of 400 to 1200° C. The moldings can be used as catalyst supports for the production of unsaturated esters from olefins, organic acids and oxygen in the gas phase and and can be used in particular for the production of vinyl acetate monomer.

8 Claims, 4 Drawing Sheets

MOLDINGS BASED ON SILICA

CROSS-REFERENCE TO RELATED APPLICATION

This application is based on German Application DE 198 28 491.8, filed Jun. 26, 1998, which disclosure is incorporated herein by reference.

FIELD OF THE INVENTION

This invention relates to moldings based on silica, to a process for their production, and their use as a catalyst for the acetoxylation of olefines.

BACKGROUND OF THE INVENTION

Silicas, particularly pyrogenic silicas, are characterized by their extremely finely divided state and their correspondingly high specific surface, by their very high purity, by their spherical particles and by the absence of pores. Due to these properties, there is an increasing interest in pyrogenic silicas as supports for catalysts (D. Koth, H. Ferch, Chem. Ing. Techn. 52, 628 (1980)).

It is known from DE-B 21 00 778 that granular materials based on pyrogenic silicas can be used as catalyst supports for the production of vinyl acetate monomer.

It is known from DE-A 38 03 900 that cylindrical particles which have arched end faces and which are based on pyrogenic silicas can be used as catalyst supports for the production of vinyl acetate monomer.

A process for the production of pressed parts is known from DE-A 39 12 504 in which aluminum stearate, magnesium stearate and/or graphite are used as a lubricant, and in which urea as well as methyl cellulose are used as pore forming agents.

These known pressed parts which are produced with magnesium stearate are commercially available as Aerosil Tablets No. 350, as supplied by Degussa. They contain about 0.4% by weight Mg.

Catalyst supports for catalysts for the synthesis of vinyl acetate monomer are known from EP 0 004 079 which consist of extruded sections with a star-shaped cross-section or which consist of ribbed lengths.

Catalysts for the synthesis of vinyl acetate monomer, which comprise at least one passageway channel with an inside diameter of at least 1 mm, are known from EP-B 464 633.

DE-A 195 38 799 describes a catalyst support in the shape of a honeycomb which predominantly consists of $SiO_2$. According to Example 1 of said patent, this support has a diameter of 25 mm, a stay width of 1 mm, a stay spacing of 2 mm, and a length of 150 mm. After being coated with catalytically active elements, the resulting catalyst can be used for the production of unsaturated esters from olefins, acids and oxygen in the gas phase, for the purification of off-gas contaminated by organic substances, and for the alkylation of aromatic compounds.

WO 97/36679 also describes a catalyst support in the shape of a honeycomb, which is coated with $SiO_2$ and which, after impregnation with palladium and gold and after activation with potassium acetate, can be used for the production of unsaturated esters.

Honeycomb-shaped catalysts are characterized by a very low pressure drop. However, the use of honeycomb-shaped catalysts in industrial reactors, particularly in tube bundle reactors, results in problems which are not inconsiderable, particularly with regard to packing tube reactors. With tube reactors, it is sometimes necessary to pack several thousand tubes of an industrial installation with honeycomb catalysts. In the course of this procedure, it has to be ensured that the honeycomb bodies do not break down during filling. Considerable emphasis has to be placed on the avoidance of edge flow effects, since otherwise the catalysts are not capable of contributing their full effect. Moreover, honeycomb-shaped catalyst materials exhibit poor thermal condutivity in a radial direction. This is particularly disadvantageous in reactions in which there is considerable evolution of heat, as in oxidation reactions for example. For the aforementioned reasons, there is currently no known industrial application in which a tube bundle reactor or thousands of tubes are operated with honeycomb-shaped catalyst materials. For this reason, reactors are packed with moldings in the form of pellets, which likewise exhibit a low pressure drop.

It is known from EP-B 0 519 435 that $SiO_2$ can be pressed by means of binders to produce supports, followed by calcining the supports obtained and washing the calcined support particles with acid until cations from the binder are no longer released. In addition, a supported catalyst, a process for the production thereof, and the use thereof for the production of vinyl acetate are also described.

EP-A 0 807 615 describes pressed parts based on pyrogenic silica. These pressed parts can be used as a catalyst or catalyst support for the production of vinyl acetate monomer and for the hydration of ethylene. The pressed parts may be of different shapes, e.g. cylindrical, spherical or annular, with an outside diameter of 0.8 to 20 mm.

SUMMARY OF THE INVENTION

The present invention relates to moldings based on silica, which are characterized in that that the supporting geometry consists of a hollow cylindrical configuration with internal reinforcing stays or spokes leading from the inner wall of the hollow cylinder to the center of the molding, or is characterized by a multiplicity of passageway channels.

The moldings according to the invention can have an outside diameter from 1 to 25 mm and a ratio of height to diameter of 0.2 to 5. Furthermore, they can have a total pore volume of 0.3 to 1.8 ml/g and a BET specific surface of 5 to 400 $m^2/g$.

The $SiO_2$ content of the moldings according to the invention is preferably more than 99.0% by weight. The proportion of other constituents can be less than 0.2% by weight. The moldings according to the invention can therefore be characterized as being free from binders. The fines can amount to less than 5% by weight. The bulk density can range from 100 to 700 g/l.

The present invention further relates to a process for the production of moldings based on silica, which is characterized in that silica is subjected to a kneading and working process, and is then extruded. The extrudate is optionally cut to the desired length by means of a cutting device, is dried at a temperature of 20 to 150° C., and is annealed for a period from 0.5 to 10 hours at a temperature from 400 to 1200° C.

In one particular embodiment of the invention, the silica can be a pyrogenic silica. Silica which can be used according to the invention, which thus includes pyrogenic silica, is described in Ullmanns Enzyklopädie der technischen Chemie, 4th Edition, Volume 21, pages 451 to 476 (1982).

One preferred embodiment of the invention is a process for the production of moldings based on silica, which is characterized in that silica is homogenized with methyl hydroxyethyl cellulose, wax and/or polyethylene glycol with the addition of water and optionally with the addition of an aqueous alkaline ammonia solution, is subjected to a kneading and working process, shaped and/or extruded. The moldings are optionally cut to the desired length by means of a cutting device, are dried at a temperature from 10 to 150° C. and are annealed for a period from 30 minutes to 10 hours at a temperature from 400 to 1200° C.

Kneaders, mixers or mills which enable good homogenization and compaction of the mixed material to be effected, such as blade mixers, fluidized bed mixers, rotary mixers or air jet mixers, for example, can be used for carrying out the process according to the invention. In particular, mixers can be used which make it possible to effect additional compaction of the mixed material, such as plough mixers, kneaders, pan grinders or ball mills. Mixing and kneading can also be effected directly in the extruder. The production of the moldings can be effected in single-screw or twin-screw extruders, in extrusion presses or in tabletting machines. The moldings according to the invention are preferably produced by means of extruders.

In one particular embodiment of the invention, the mixture can have the following composition before it is shaped:
50–90% by weight silica, preferably 65–85% by weight;
0.1–20% by weight methyl hydroxyethyl cellulose, preferably 5–15% by weight;
0.1–15% wax, preferably 5–12% by weight;
0.1–15% polyethylene glycol, preferably 5–10% by weight.

The moldings can be annealed at 400–1200° C. for 30 minutes to 10 hours. The fracture strength, total specific surface and the pore volume can be varied within certain limits by varying the amounts of substances used and by varying the pressing pressure.

The moldings according to the invention can be used either directly as a catalyst or as a catalyst support.

For use as a catalyst support, the moldings can be brought into contact with a catalytically active substance after their production and can be activated, if necessary, by suitable further treatment.

In particular, moldings made from pyrogenic silica can be used as a support for the catalyst for the production of vinyl acetate monomer from ethylene, acetic acid and oxygen.

The moldings according to the invention comprise the following properties or enable such properties to be obtained:
low pressure drops
low bulk density
relatively large external surface per unit volume of a reaction vessel
improved mass and heat transfer
comparatively simple packing and emptying of industrial tube bundle reactors, particularly by comparison with known honeycomb-shaped catalysts.

The low pressure drop across moldings according to the invention results, amongst other causes, from their geometric dimensions, due to which there is an extremely high free surface area over the cross-section of the moldings and/or a very high voids fraction in the catalyst packing.

Catalysts can be produced based on moldings according to the invention which enable higher space-time yields and selectivities to be achieved.

The invention is explained in greater detail below with reference to the drawings.

DETAILED DESCRIPTION OF THE PREFERRED EMBODIMENTS

Figure 1:
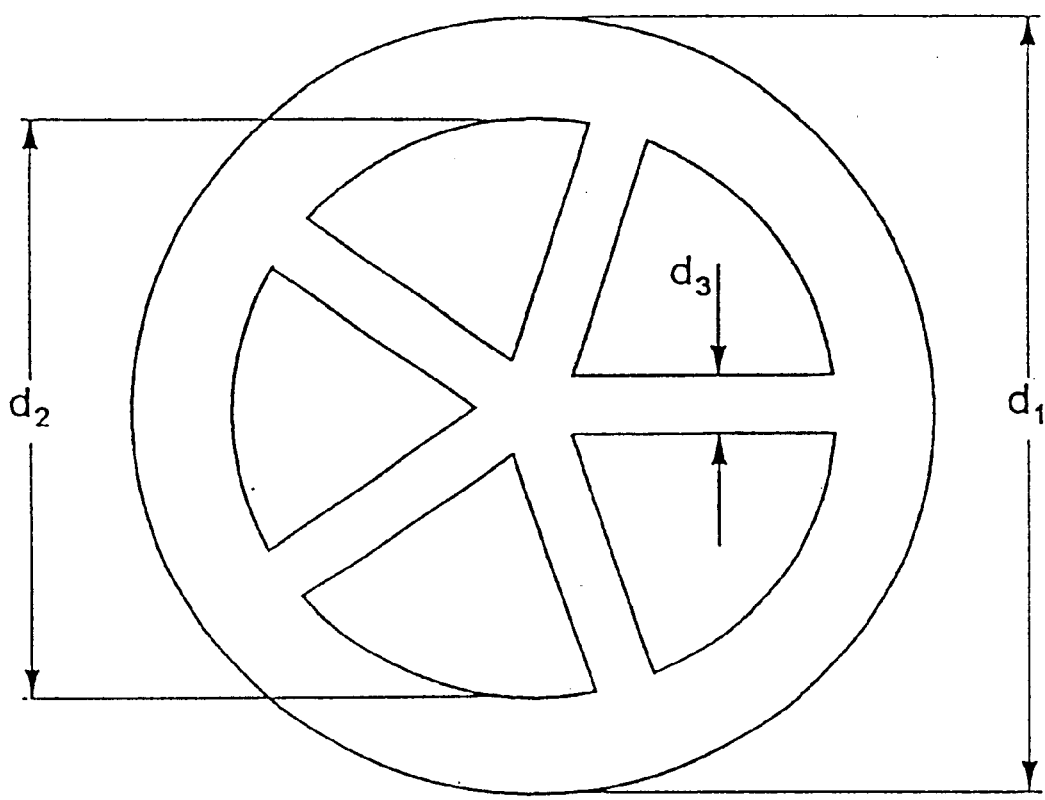
FIG. 1 is a cross-section through a pressed part or supported catalyst in the shape of a cartwheel.
Figure 2:
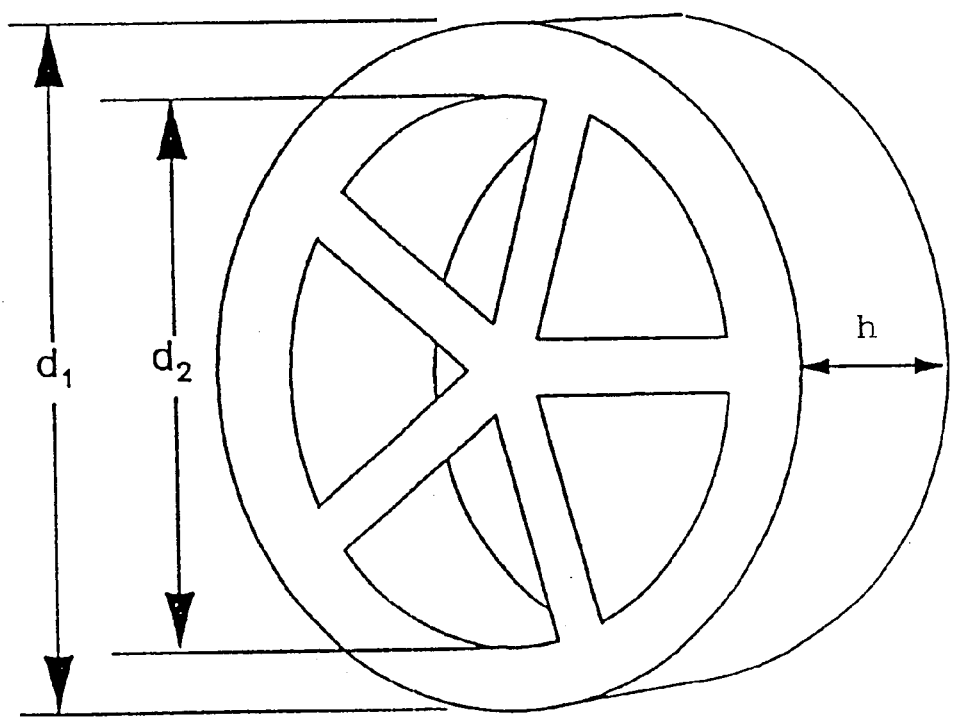
FIG. 2 is a perspective view of the cartwheel shape shown in FIG. 1.
Figure 3:
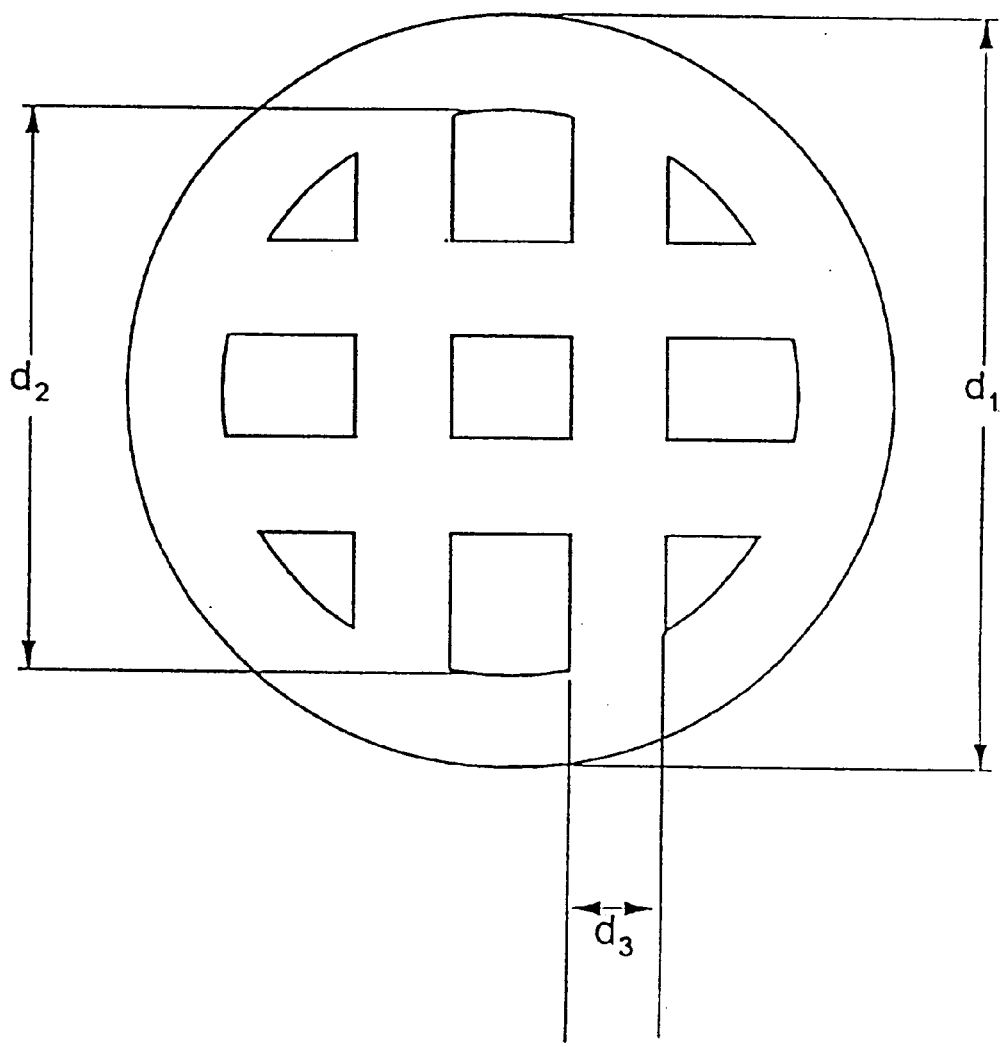
FIG. 3 shows a pressed part or supported catalyst in the shape of what is termed a minilith.
Figure 4:
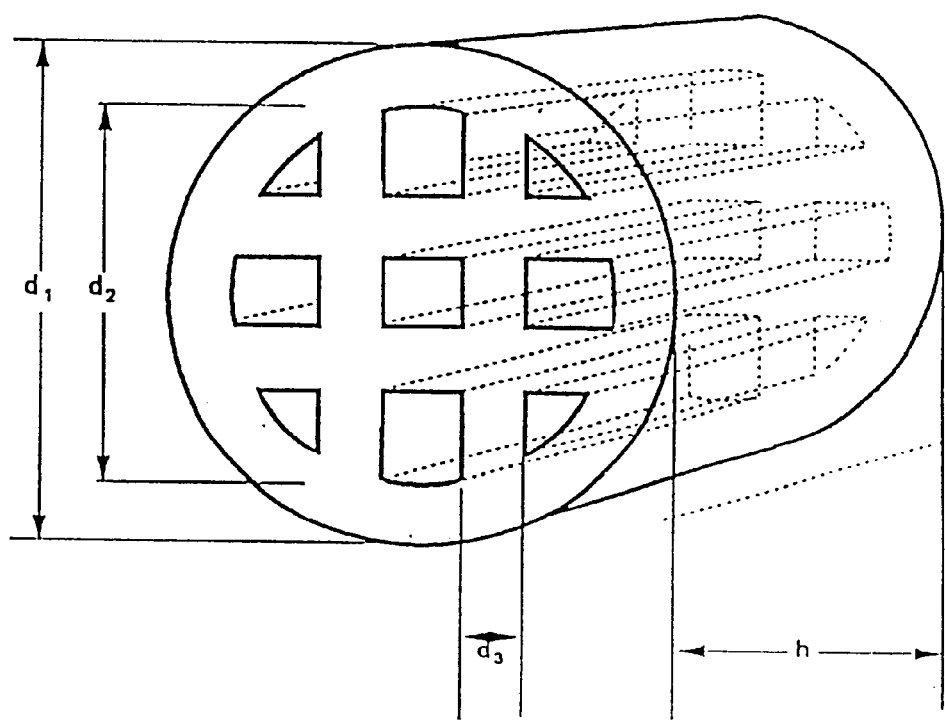
FIG. 4 is a perspective view of the minilith shown in FIG. 3.

FIGS. 1–4 illustrate embodiments of the invention. The maximum outside diameter $d_1$ of the cartwheel shaped supports, shown in FIGS. 1 and 2, and of what are termed miniliths, shown in FIGS. 3 and 4, is preferably 25 mm, wherein the ratio of height h to outside diameter $(h/d_1)$ can range from 0.2 to 5. The inside diameter of the moldings is denoted by $d_2$. The wall thickness the moldings $((d_1-d_2) \times 0.5)$ can fall within the range from 0.05 to 0.3 times the outside diameter. The stay or spoke thickness of the moldings is denoted by $d_3$ and can fall within the range from 0.05 to 0.3 times the outside diameter. The number of internal reinforcing stays or spokes or passageway channels can amount to at least 3.

The present invention also relates to a supported catalyst for the production of vinyl acetate monomer (VAM), which catalyst contains, as catalytically active components on a support (molding), palladium and/or compounds thereof and alkali compounds, and which additionally contains gold and/or compounds thereof (Pd/alkali/Au system) or cadmium and/or compounds thereof (Pd/alkali/Cd system) or barium and/or compounds thereof (Pd/alkali/Ba system) or palladium, alkali compounds and mixtures of gold and/or cadmium and/or barium, and which is characterized in that the support is a molding according to the invention.

Potassium compounds, such as potassium acetate for example, are preferably used as alkali compounds.

The catalytically active components can be present in the following systems:
Pd/Au/alkali compounds
Pd/Cd/alkali compounds
Pd/Ba/alkali compounds The supported catalysts according to the invention can be used for the production of vinyl acetate monomer. For this purpose, ethylene, acetic acid and molecular oxygen or air are reacted in the gas phase, optionally with the addition of inert gases, at temperatures between 100 and 250° C. and at normal or elevated pressure in the presence of the supported catalysts according to the invention.

A production process of this type is known from the documents DE 16 68 088, U.S. Pat. No. 4,048,096, EP-A 0 519 435, EP-A 0 634 208, EP-A 0 723 810. EP-A 0 634 209, EP-A 0 632 214, EP-A 0 654 301 and EP-A 0 0807 615.

The present invention also relates to a process for the production of the supported catalyst for the production of vinyl acetate monomer by depositing Pd, Au, Cd or Ba metal compounds by impregnation, spraying, evaporation, immersion or precipitation, optionally reducing the reducible metal compounds which are deposited on the support, optionally washing in order to remove chloride fractions which may be present, impregnating with alkali acetates or with alkali compounds which under the reaction conditions for the production of vinyl acetate monomer are completely or partially converted into alkali acetates, in a suitable sequence, which is characterized in that the support is a molding according to the present invention.

The present invention further relates to a process for producing a supported catalyst for the production of vinyl acetate monomer by impregnating the support with a basic solution and a solution which contains gold and palladium salts, wherein impregnation is effected simultaneously or in succession, with or without intermediate drying, optionally washing the support in order to remove chloride fractions which may be present and reducing the insoluble compounds which are precipitated on the support before or after washing, drying the catalyst precursor which is thus obtained, and impregnating with alkali acetates or with alkali compounds which under the reaction conditions for the production of vinyl acetate monomer are completely or partially converted into alkali acetates, which is characterized in that the support is a molding based on silica having a supporting geometry that includes a hollow cylindrical configuration having internal reinforcing stays or spokes leading from the inner wall of the hollow cylinder to the center of the molding or that has a multiplicity of passageway channels.

The supported catalysts according to the invention can be used for the production of unsaturated esters from olefins, organic acids and oxygen in the gas phase.

The catalysts of the Pd/alkali/Au system according to the invention can be obtained by impregnating the support with a basic solution and with a solution which contains gold and palladium salts, wherein the impregnation steps can be carried out simultaneously or in succession, with or without intermediate drying. The support is subsequently washed in order to remove chloride fractions which may be present. The insoluble metal compounds which are precipitated on the support can be reduced before or after washing. The catalyst precursor which is thus obtained can be dried in order to activate the catalyst and can be impregnated with alkali acetates or with alkali compounds which under the reactions conditions for the production of vinyl acetate monomer are completely or partially converted into alkali acetates. In general, the noble metals of Pd/Au catalysts can be present in the form of a shell on the support.

For Pd/alkali/Ba catalysts, the metal salts can be deposited by impregnating, spraying, immersion or precipitation (EP 0 519 436). The same methods are known for Pd/alkali/Cd catalysts (U.S. Pat. No. 4,902,823, U.S. Pat. No. 3,393,199, U.S. Pat. No. 4,668,819).

Depending on the catalyst system, the supported catalyst can be reduced.

Reduction of the catalyst can be effected in an aqueous phase or in the gas phase. Formaldehyde or hydrazine are suitable for reduction in an aqueous phase, for example.

Reduction in the gas phase can be effected with hydrogen or forming gas (95% by volume $N_2$+5% by volume $H_2$), ethylene or ethylene diluted with nitrogen. Reduction with hydrogen can be conducted at temperatures between 40 and 260° C., preferably between 70 and 200° C. Reduction with forming gas (95% by volume $N_2$ and 5% by volume $H_2$) can be conducted at temperatures between 300 and 550° C., preferably between 350 and 500° C. The catalyst can also be reduced with ethylene in the production reactor, after activation with alkali acetate.

The catalyst supports according to the invention advantageously retain their mechanical strength under the reaction conditions of the catalytic process, particularly under the effect of acetic acid.

The production of supported catalysts of the Pd/alkali/Au system on moldings according to the invention is described in greater detail below.

The moldings according to the invention are impregnated with a solution which contains palladium and gold. Simultaneously with the solution which contains noble metals, or in any desired sequence in succession, the moldings according to the invention are impregnated with a basic solution which may contain one or more basic compounds. The basic compound or compounds serve to convert palladium and gold into their hydroxides.

The compounds in the basic solution may consist of alkali hydroxides, alkali bicarbonates, alkali carbonates, alkali silicates or mixtures of these substances. Potassium hydroxide and/or sodium hydroxide are preferably used.

Palladium chloride, sodium or potassium palladium chloride or palladium nitrate, for example, can be used as palladium salts for the production of the solution which contains noble metals. Gold(III) chloride and tetrachloroauric(III) acid can be used as gold salts. Potassium palladium chloride, sodium palladium chloride and/or tetrachloroauric acid are preferably used.

Impregnation of the moldings according to the invention with the basic solution has an effect on the deposition of the noble metals in the support material. The basic solution can be used either simultaneously with the solution of noble metal or can be used in any desired sequence with this solution. The moldings according to the invention are brought into contact with the basic solution and with the solution of noble metal either simultaneously or in any desired sequence in succession. When the moldings according to the invention are impregnated in succession with the two solutions, an intermediate drying step can be carried out after the first impregnation step.

The pressed parts according to the invention are preferably first impregnated with the basic compound. Subsequent impregnation with the solution which contains palladium and gold results in the precipitation of palladium and gold in a surface shell on the molding. The reverse sequence of impregnation generally results in a more or less homogeneous distribution of the noble metals over the cross-section of the molding used. When the process is conducted appropriately, however, catalysts comprising a defined shell can also be obtained when employing the reverse sequence of impregnation (see U.S. Pat. No. 4,048,096 for example). Catalysts which comprise a homogeneous or almost homogeneous distribution of noble metal generally exhibit reduced activity and selectivity.

Catalysts with shell thicknesses less than 1 mm are particularly suitable. The shell thickness is influenced by the amount of basic compound which is deposited on the molding in relation to the desired amount of noble metal. The higher this ratio is, the lower is the thickness of the shell which is formed. The quantitative ratio of basic compound to noble metal compounds which is necessary for a desired shell thickness depends on the nature of the molding and on the basic compound and noble metal compounds which are selected. The requisite quantitative ratio is advisedly determined by a few preliminary tests. The shell thickness which is present can easily be determined in such tests by cutting open the catalyst particles.

The minimum necessary amount of basic compound results from the stoichiometrically calculated amount of hydroxide ions which are necessary for the conversion of the palladium and gold in the hydroxide. As an approximate value, the basic compound should be used in a 1 to 10-fold stoichiometric excess for a shell thickness of 0.5 mm.

After the pore volume impregnation process, the moldings according to the invention can be coated with the basic compounds and with noble metal salts. If intermediate drying is employed, the volume of both solutions is selected so that they each correspond to about 90 to 100% of the absorption capacity of the molding used. If intermediate drying is omitted, the sum of the individual volumes of the two impregnation solutions has to correspond to the above condition, wherein the individual volumes can be in a ratio of 1:9 to 9:1 to each other. A volume ratio from 3:7 to 7:3 is preferably employed, particularly a ratio of 1:1. Water is preferably used as the solvent in both these cases. Suitable organic or aqueous-organic solvents can also be used.

The reaction of the noble metal salt solution with the basic solution to form insoluble noble metal compounds occurs slowly and is generally complete after 1 to 24 hours, depending on the method of preparation. Thereafter, the water-insoluble noble metal compounds are treated with reducing agents. Wet reduction can be effected, with aqueous hydrazine hydrate for example, or a gas phase reduction can be effected with hydrogen, ethylene, forming gas or methanol vapour. Reduction can be effected at normal temperature or at an elevated temperature, and at normal pressure or under an elevated pressure, optionally with the addition of inert oases also.

Before and/or after the reduction of the noble metal compounds, any chloride which may be present on the molding is removed by thoroughly washing the molding. After washing, the molding should contain less than 500 ppm, preferably less than 200 ppm, of chloride.

The molding which is obtained after reduction as a catalyst precursor is dried and is subsequently impregnated with alkali acetates or with alkali compounds which under the reaction conditions for the production of vinyl acetate monomer are completely or partially converted into alkali acetates. The molding is preferably impregnated with potassium acetate. A pore volume impregnation method is preferably used again here. This means that the requisite amount of potassium acetate is dissolved in a solvent, preferably water, the volume of which approximately corresponds to the absorption capacity of the molding for the selected solvent. This volume is approximately equal to the total pore volume of the moldings.

The finished, coated molding is subsequently dried to a residual moisture content of less than 2%. Drying can be effected in air, or can also optionally be effected under nitrogen as an inert gas.

The production of supported catalysts of the Pd/alkali/Cd or Pd/alkali/Ba systems on moldings according to the invention is effected in a known manner according to the patent specifications cited above.

For the synthesis of vinyl acetate monomer it is advisable to coat the moldings with 0.2 to 4 preferably 0.3 to 3%, by weight palladium, 0.1 to 2, preferably 0.15 to 1.5%, by weight gold and 1 to 10, preferably 1.5 to 9%, by weight potassium acetate, with respect to the weight of the molding used in each case. These data are applicable to the Pd/alkali/Au system. In the case of moldings with a bulk density of 500 g/l, these concentration data correspond to volume-based concentrations of 1.0 to 20 g/l palladium, 0.5 to 10 g/l gold and 5 to 50 g/l potassium acetate. In order to prepare the impregnation solution, the corresponding amounts of palladium and gold compounds are dissolved in a volume of water which approximately corresponds to 90–100% of the water absorption capacity of the molding in question. The same procedure is employed for the preparation of the basic solution.

The cadmium content of the Pd/alkali/Cd catalyst (finished, coated molding) can generally range from 0.1 to 2.5% by weight, preferably 0.4 to 2.0% by weight.

The barium content of the Pd/alkali/Ba catalyst (finished, coated molding) can generally range from 0.1 to 2.0% by weight, preferably 0.4 to 1.8% by weight.

The palladium content of the Pd/alkali/Cd or Pd/alkali/Ba catalyst (finished, coated molding) can generally range from 0.2 to 4% by weight, preferably 0.3 to 3% by weight palladium.

The potassium acetate content of the Pd/alkali/Cd or Pd/alkali/Ba catalyst (finished, coated molding) can generally range from 1 to 10% by weight, preferably 1.5 to 9% by weight.

Silicas which have the following physical and chemical properties, and which are also known by the name AEROSIL®, manufactured by Degussa-Hüls AG (Germany), can be used as pyrogenic silicas:

| AEROSIL ® silica | OX 50 | 90 | 130 | 150 | 200 | 300 | 380 |
|---|---|---|---|---|---|---|---|
| BET specific surface m$^2$/g | 50 ± 15 | 90 ± 15 | 130 ± 25 | 150 ± 15 | 200 ± 25 | 300 ± 30 | 380 ± 30 |
| Average size of primary particles nm | 40 | 20 | 16 | 14 | 12 | 7 | 7 |
| Tamped density[1] g/l | about 130 | about 80 | about 50 | about 50 | about 50 | about 50 | about 50 |
| Loss on drying[2] (2 hours at 105° C.) | <1.5 | <1 | <1.5 | <0.5 | <1.5 | <1.5 | <1.5 |
| Loss on ignition[2][5] (2 hours at 1000° C.) | <1 | <1 | <1 | <1 | <1 | <2 | <2.5 |
| pH[3] (in a 4% aqueous dispersion) | 3.8–4.8 | 3.6–4.5 | 3.6–4.3 | 3.6–4.3 | 3.6–4.3 | 3.6–4.3 | 3.6–4.3 |
| SiO$_2$[6] % wt. | >99.8 | >99.8 | >99.8 | >99.8 | >99.8 | >99.8 | >99.8 |
| Al$_2$O$_3$[6] % wt. | <0.08 | <0.05 | <0.05 | <0.05 | <0.05 | <0.05 | <0.05 |
| Fe$_2$O$_3$[6] % wt. | <0.01 | <0.003 | <0.003 | <0.003 | <0.003 | <0.003 | <0.003 |
| TiO$_2$[6] % wt. | <0.03 | <0.03 | <0.03 | <0.03 | <0.03 | <0.03 | <0.03 |
| HCl[6][7] % wt. | <0.025 | <0.025 | <0.025 | <0.025 | <0.025 | <0.025 | <0.025 |
| Residue on sieve[4] % wt. (Mocker, 45 μm) | <0.02 | <0.05 | <0.05 | <0.05 | <0.05 | <0.05 | <0.05 |

[1] according to DIN 53 194
[2] according to DIN 55 921
[3] according to DIN 53 200
[4] according to DIN 53 580
[5] with respect to the substance dried for 2 hours at 105° C.
[6] with respect to the substance calcined for 2 hours at 1000° C.
[7] The HCl content is a constituent of the loss on ignition In order to produce AEROSIL®, a volatile silicon compound is injected through a nozzle into an oxyhydrogen gas flame formed from hydrogen and air. Silicon tetrachloride is used in most cases. This compound hydrolyzes to form silica and hydrochloric acid under the effect of the water formed during the oxyhydrogen gas reaction. After leaving the flame, the silica enters what is termed a coagulation zone, in which the AEROSIL® primary particles and primary aggregates agglomerate The product, which at this stage is present as a kind of aerosol, is separated from the accompanying gaseous substances in cyclones, and is subsequently post-treated with moist hot air. The residual content of hydrochloric acid can be reduced to less than 0.025% by this procedure. Since at the end of this process the AEROSIL® only has a bulk density of about 15 g/l, it is subjected to a subsequent vacuum compaction step by means of which tamped densities of about 50 g/l or more can be achieved.

The particle size of products obtained in this manner can be varied by varying the reaction conditions, such as the flame temperature, the content of hydrogen or oxygen, the amount of silicon tetrachloride, the residence time in the flame or the length of the coagulation section, for example.

The BET specific surface is determined using nitrogen according to DIN 66 131. The pore volume is determined by calculation from the sum of the micro-, meso- and macropore volumes.

Determination of the micro- and mesopores is effected by plotting an $N_2$ isotherm and evaluating the isotherm by the BET, de Boer and Barret, Joyner or Halenda methods.

The macropores are determined by the Hg penetration method.

The invention is further explained by the Examples given below.

EXAMPLE 1

85% by weight AEROSIL® 200
5% by weight methyl hydroxyethyl cellulose
5% by weight wax
5% by weight polyethylene glycol
were compacted in a kneader, with the addition of water which had been made slightly alkaline with an aqueous alkaline ammonia solution (15 ml of a 32% solution for a 2 kg batch). The kneaded material was shaped in a single-screw extruder to form hollow cylindrical extrudates in the shape of so-called cartwheels comprising five internal reinforcing spokes or stays leading from the inner wall of the hollow cylinder to the center of the molding, and was cut to the desired length of 3.5 to 5.5 mm by a cutting device. The moldings were dried on a belt drier at 90° C. and were subsequently calcined for 6 hours at 900° C.

The moldings obtained had the following physical and chemical properties:

| Molding dimensions: | |
| --- | --- |
| outside diameter (mm) | 7.5 ± 0.5 |
| height(mm) | 4.5 ± 1 |
| Wall thickness: | 1.3 ± 0.05 |
| Stay width: | 1.3 ± 0.05 |
| BET specific surface ($m^2/g$) | 79 |
| Pore volume (ml/g) | 0.69 |
| Bulk density (g/l) | 398 |
| $SiO_2$ content (% by weight) | 99.9 |
| Height/diameter ratio | 0.6 |

EXAMPLE 2

85% by weight AEROSIL® 200
5% by weight methyl hydroxyethyl cellulose
5% by weight wax
5% by weight polyethylene glycol
were compacted in a kneader, with the addition of water which had been made slightly alkaline with an aqueous alkaline ammonia solution (15 ml of a 32% solution for a 2 kg batch). The kneaded material was shaped in a single-screw extruder to form hollow cylindrical extrudates in the shape of so-called cartwheels comprising five internal reinforcing spokes or stays leading from the inner wall of the hollow cylinder to the center of the molding, and was cut to the desired length of 5.5 to 6.5 mm by a cutting device. The moldings were dried on a belt drier at 90° C. and were subsequently calcined for 6 hours at 850° C.

The moldings obtained had the following physical and chemical properties:

| Molding dimensions: | |
| --- | --- |
| outside diameter (mm) | 6.0 ± 0.2 |
| height (mm) | 6.0 ± 0.5 |
| Wall thickness: | 0.95 ± 0.05 |
| Stay width: | 0.95 ± 0.05 |
| BET specific surface ($m^2/g$) | 148 |
| Pore volume (ml/g) | 0.75 |
| Bulk density (g/l) | 390 |
| $SiO_2$ content (% by weight) | 99.9 |
| Height/diameter ratio | 1.0 |

EXAMPLE 3

85% by weight AEROSIL® 200
5% by weight methyl hydroxyethyl cellulose
5% by weight wax
5% by weight polyethylene glycol
were compacted in a kneader, with the addition of water which had been made slightly alkaline with an aqueous alkaline ammonia solution (15 ml of a 32% solution for a 2 kg batch). The kneaded material was shaped in a single-screw extruder to form hollow cylindrical extrudates in the shape of so-called cartwheels comprising five internal reinforcing spokes or stays leading from the inner wall of the hollow cylinder to the center of the molding, and was cut to the desired length of 3.5 to 5.5 mm by a cutting device. The moldings were dried on a belt drier at 90° C. and were subsequently calcined for 6 hours at 800° C.

The moldings obtained had the following physical and chemical properties:

| Molding dimensions: | |
| --- | --- |
| outside diameter (mm) | 7.5 ± 0.5 |
| height(mm) | 4.5 ± 1 |
| Wall thickness: | 1.3 ± 0.05 |
| Stay width: | 1.3 ± 0.05 |
| BFT specific surface ($m^2/g$) | 170 |
| Pore volume (ml/g) | 0.9 |
| Bulk density (g/l) | 360 |
| $SiO_2$ content (% by weight) | 99.9 |
| Height/diameter ratio | 0.6 |

EXAMPLE 4

85% by weight AEROSIL® 200
5% by weight methyl hydroxyethyl cellulose
5% by weight wax
5% by weight polyethylene glycol
were compacted in a kneader, with the addition of water which had been made slightly alkaline with an aqueous alkaline ammonia solution (15 ml of a 32% solution for a 2 kg batch). The kneaded material was shaped in a single-screw extruder to form hollow cylindrical extrudates in the shape of so-called cartwheels comprising five internal reinforcing spokes or stays leading from the inner wall of the hollow cylinder to the center of the molding, and was cut to the desired length of 5.5 to 6.5 mm by a cutting device. The moldings were dried on a belt drier at 90° C. and were subsequently calcined for 6 hours at 800° C.

The moldings obtained had the following physical and chemical properties:

| Molding dimensions: | |
| --- | --- |
| outside diameter (mm) | 6.0 ± 0.2 |
| height(mm) | 6.0 ± 0.5 |
| Wall thickness: | 0.95 ± 0.05 |
| Stay widtb: | 0.95 ± 0.05 |
| BBT specific surface (m$^2$/g) | 170 |
| Pore volume (ml/g) | 0.9 |
| Bulk density (g/l) | 350 |
| SiO$_2$ content (% by weight) | 99.9 |
| Height/diameter ratio | 1.0 |

EXAMPLE 5

85% by weight AEROSIL® 200
5% by weight methyl hydroxyethyl cellulose
5% by weight wax
5% by weight polyethylene glycol
were compacted in a kneader, with the addition of water which had been made slightly alkaline with an aqueous alkaline ammonia solution (15 ml of a 32% solution for a 2 kg batch). The kneaded material was shaped in a single-screw extruder to form hollow cylindrical extrudates in the shape of what are termed miniliths as shown in FIGS. 3 and 4, comprising nine passageway channels, and was cut to the desired length of 4 to 5 mm by a cutting device. The moldings were dried on a belt drier at 90° C. and were subsequently calcined at 800° C.

The moldings obtained had the following physical and chemical properties:

| Molding dimensions: | |
| --- | --- |
| outside diameter (mm) | 5.8 ± 0.2 |
| height(mm) | 4.5 ± 0.5 |
| Wall thickness: | 0.8 ± 0.05 |
| Stay width: | 0.8 ± 0.05 |
| BET specific surface (m$^2$/g) | 170 |
| Pore volume (ml/g) | 0.9 |
| Bulk density (g/l) | 350 |
| SiO$_2$ content (% by weight) | 99.9 |
| Height/diameter ratio | 0.78 |

COMPARATIVE EXAMPLE 1

A palladium-gold-potassium acetate catalyst was prepared according to Example 11 of EP 0 807 615 A1. The catalyst support which was used was a molding according to Example 5 of EP 0 807 615 A1, but which had the dimensions 8×5×3 mm (outside diameter×height×inside diameter) and which had faceted edges.

The concentrations of the impregnation solutions were selected so that the finished catalyst contained a concentration of 0.55% by weight palladium, 0.25% by weight gold and 5.0% by weight potassium acetate.

In a first step, the support was first of all impregnated with a basic solution of sodium hydroxide in water. The volume of the aqueous NaOH solution corresponded to 50 percent of the water absorption capacity of the dry support. After impregnation with sodium hydroxide, the support was immediately impregnated, without intermediate drying, with an aqueous solution of noble metals comprising sodium palladium chloride and tetrachloroauric acid, the volume of which likewise corresponded to 50 percent of the water absorption capacity of the dry support.

After a holding time of 1.5 hours, during which the noble metal compounds were hydrolyzed, the support particles were washed until they were free from chloride. The support particles were dried and were reduced at 450° C. in the gas phase with forming gas (95% by volume N$_2$, 5% by volume H$_2$). Thereafter, the catalyst was impregnated with an aqueous solution of potassium acetate and was dried again. Drying was effected in the gas phase with nitrogen.

The sodium hydroxide concentration of the basic solution was calculated so that a shell which contained noble metals and which was formed on the support particles had a thickness <1.0 mm.

EXAMPLE 6

A palladium-gold-potassium acetate catalyst as described in Comparative Example 1 was produced on the molding according to the invention according to Example 1.

EXAMPLE 7

A palladium-gold-potassium acetate catalyst as described in Comparative Example 1 was produced on the molding according to the invention according to Example 2.

EXAMPLE OF USE 1

The activity and selectivity of the catalysts from Comparative Example 1 and from Examples 6 and 7 were measured during a test procedure which had a duration of up to 24 hours.

The catalysts were tested with the following gas composition: 75% by volume ethylene, 16.6% by volume acetic acid, 8.3% by volume oxygen, in an oil-heated tubular flow reactor (reactor length 710 mm, inside diameter 23.7 mm) at normal pressure and at a space velocity (GHSV) of 400 h$^{-1}$. The catalysts were investigated over the temperature range from 120 to 165° C., as measured in the catalyst bed.

The reaction products were analyzed at the outlet of the reactor by means of on-line gas chromatography. The space-time yield of the catalyst in grams of vinyl acetate monomer per hour per kilogram of catalyst (g VAM/(h×kg$_{cat}$) was determined as a measure of the catalyst activity.

The carbon dioxide which was formed by the combustion of ethylene was also determined and was employed for assessing the selectivity of the catalyst.

The test results on catalysts from Comparative Example 1 and from Examples 6 and 7 are presented in Table 1. The catalyst activity and the catalyst selectivity of the catalyst according to Comparative Example 1 were taken as 100 percent.

The results shown in Table 1 demonstrate that the catalysts according to the invention, which are based on the moldings according to the invention, exhibit a significantly higher activity than that of the known comparative catalyst, whilst exhibiting a comparable selectivity or even an improved selectivity.

TABLE 1

| Catalyst | Activity g VAM/(h × kg$_{cat.}$) in % of Comp. Ex. 1 | Selectivity CO$_2$ in the off-gas in % per unit area in % of Comp. Ex. 1 | Catalyst temperature ° C. |
|---|---|---|---|
| Comp. ex. 1 | 100 | 100(3.2) | 146.4 |
| B6 | 84.5 | 56.3 | 131.8 |
| | 108.5 | 84.4 | 143.5 |
| | 123.5 | 87.5 | 149.9 |
| B7 | 104.1 | 65.6 | 132.2 |
| | 135.3 | 75.0 | 144.7 |
| | 153.7 | 103.1 | 152.0 |

What is claimed is:

1. A molding based on silica, comprising pyrogenic silica in a hollow cylindrical configuration having a structure selected from the group consisting of internal reinforcing stays or spokes leading from an inner wall of a hollow cylinder to a center of the molding and a hollow cylinder having a multiplicity of channels forming passageways therethrough, wherein the molding has a diameter from 1 to 25 mm and a ratio of height to diameter from 0.2 to 5.

2. A molding according to claim 1, wherein the molding has a wall thickness within the range from 0.05 to 0.3 times the diameter and a stay or spoke thickness within the range from 0.05 to 0.3 times the diameter.

3. A molding according to claim 1, wherein the number of internal reinforcing stays or spokes or passageway channels is at least 3.

4. A process for the production of moldings based on silica according to claim 1, comprising:

kneading and shaping the silica;

extruding the kneaded, shaped silica;

optionally cutting the extrudate by means of a cutting device;

drying at a temperature of 20 to 150° C.; and annealing for a period of from 0.5 to 10 hours at a temperature of from 400 to 1200° C.

5. A process for the production of moldings based on silica according to claim 1, comprising:

homogenizing the silica with at least one member selected from the group consisting of methyl hydroxyethyl cellulose, wax and polyethylene glycol, with the addition of water and optionally with the addition of an aqueous alkaline ammonia solution, kneading and shaping or extruding the moldings, optionally cutting the moldings by means of a cutting device;

drying the moldings at a temperature from 10 to 150° C.; and annealing for a period of from 30 minutes to 10 hours at a temperature of from 400 to 1200° C.

6. A supported catalyst for the production of vinyl acetate monomer (VAM), which catalyst comprises, as catalytically active components on a support, at least one member selected from the group consisting of palladium and palladium compounds, together with alkali compounds, and which additionally comprises at least one member selected from the group consisting of gold, gold compounds, cadmium, cadmium compounds, barium and barium compounds, wherein the support is a molding according to claim 1.

7. A process for the production of the supported catalyst according to claim 6 for the production of vinyl acetate monomer comprising:

depositing Pd, Au, Cd or Ba metal compounds on a support by impregnation, spraying, evaporation, immersion or precipitation, optionally reducing the metal compounds which are deposited on the support, optionally washing in order to remove chloride fractions which may be present, impregnating with alkali acetates or with alkali compounds which under reaction conditions for the production of vinyl acetate monomer are completely or partially converted into alkali acetates.

8. A process for the production of the supported catalyst according to claim 6 for the production of vinyl acetate monomer comprising:

impregnating the support with a basic solution and with a solution which contains gold and palladium salts, wherein impregnation is effected simultaneously or in succession, with or without intermediate drying, optionally washing the support in order to remove chloride fractions which may be present, reducing insoluble compounds which are precipitated on the support before or after washing, drying catalyst precursor which is thus obtained, and impregnating with alkali acetates or with alkali compounds which, under reaction conditions for the production of vinyl acetate monomer, are completely or partially converted into alkali acetates.

* * * * *